United States Patent
Bonthuys

(10) Patent No.: US 6,458,073 B1
(45) Date of Patent: Oct. 1, 2002

(54) DEVICE FOR TREATMENT OF ERECTILE DYSFUNCTION

(76) Inventor: Barend Willem Bonthuys, P.O. Box 39385, Moreletapark, 0044 (ZA)

( * ) Notice: Subject to any disclaimer, the term of this patent is extended or adjusted under 35 U.S.C. 154(b) by 0 days.

(21) Appl. No.: 09/623,241

(22) PCT Filed: Mar. 3, 1999

(86) PCT No.: PCT/US99/04736
§ 371 (c)(1),
(2), (4) Date: Aug. 30, 2000

(87) PCT Pub. No.: WO99/44550
PCT Pub. Date: Sep. 10, 1999

(30) Foreign Application Priority Data

Mar. 3, 1998 (ZA) .............................................. 98/1789

(51) Int. Cl.$^7$ ................................................. A61F 5/00
(52) U.S. Cl. ........................................................ 600/38
(58) Field of Search ........................... 600/38–41; 601/6, 601/9–11; 604/74; 222/380, 321.9, 207, 96

(56) References Cited

U.S. PATENT DOCUMENTS

| | | | | |
|---|---|---|---|---|
| 4,602,625 A | * | 7/1986 | Yachia et al. .................. | 600/40 |
| 4,892,517 A | * | 1/1990 | Yuan et al. .................... | 604/74 |
| 5,095,895 A | * | 3/1992 | Walsh .......................... | 600/39 |
| 5,213,563 A | * | 5/1993 | Cox ............................. | 600/38 |
| 5,338,288 A | * | 8/1994 | Finkle ......................... | 600/41 |
| 5,344,389 A | * | 9/1994 | Walsdorf et al. ............... | 600/39 |
| 5,421,808 A | * | 6/1995 | Osbon et al. .................. | 600/38 |
| 5,462,514 A | * | 10/1995 | Harris ......................... | 600/38 |
| 5,622,186 A | * | 4/1997 | Schwartz ...................... | 600/38 |
| 5,624,378 A | | 4/1997 | Baldecchi ..................... | 600/38 |
| 5,782,621 A | | 7/1998 | Harris ......................... | 417/470 |
| 6,036,635 A | * | 3/2000 | Altshuler ...................... | 600/38 |
| 6,248,059 B1 | * | 6/2001 | Gamper et al. ................ | 600/38 |
| 6,302,305 B1 | * | 10/2001 | Bonningue ............... | 222/321.7 |

FOREIGN PATENT DOCUMENTS

CH 347300 8/1960

OTHER PUBLICATIONS

English Translation Of CH 347300 Dated Aug. 15, 1960.

* cited by examiner

Primary Examiner—Eric F. Winakur
Assistant Examiner—Nikita Veniaminov
(74) Attorney, Agent, or Firm—Ladas & Parry

(57) ABSTRACT

A device for the treatment of erectile dysfunction or for penile exercise includes a vessel defining an elongated vacuum chamber and a mouth opening leading into the vacuum chamber. An annular pumping sleeve is mounted on, and slidingly displaceable relative to the vessel. The device includes valving arranged such that reciprocation of the sleeve relative to the vessel serves to pump air out of the vacuum chamber. The device further includes a constriction ring which is sealingly and dismountably mountable on the vessel, and which is configured sealingly to engage with an outer surface of a human penis inserted into the vacuum chamber.

19 Claims, 4 Drawing Sheets

DEVICE FOR TREATMENT OF ERECTILE DYSFUNCTION

THIS INVENTION relates to a device for the treatment of erectile dysfunction or for penile exercise in the human male. It also relates to a method of treatment of erectile dysfunction and to a method of penile exercise. It further relates to a pump device and to a sealing constriction ring.

BACKGROUND OF THE INVENTION

A problem that occasionally occurs in human male s is the inability to attain an erection of the penis.

One manner which has been used to alleviate this problem is by subjecting the penis to a negative pressure thereby inducing blood to flow into the erectile tissue of the penis and cause an erection. In order to retain the blood in the erected penis, a constriction ring is used to inhibit the flow of blood from the erect penis and thereby retain the erection of the penis. Various vacuum devices have been proposed which operate in this fashion, Inter alia, U.S. Pat. Nos. 5,213,563, 6,095,895, 5,421,808, 4,602,625 and CH 3473007.

It will be appreciated; that a device in accordance with the invention is normally used in an intimate situation. A major disadvantage with the prior art devices is that they are cumbersome and fairly time consuming to use which is not ideal in an intimate situation.

It is thus an object of the invention to provide a device which may be used particularly but not necessarily exclusively in the treatment of erectile dysfunction and for penile exercise, and which is not unwieldy or cumbersome when used in intimate situations.

BRIEF SUMMARY OF THE INVENTION

According to one aspect of the invention there is provided a device for the treatment of erectile dysfunction or for penile exercise which includes:

- a vessel defining a vacuum chamber and having a mouth opening leading into the vacuum chamber, the vacuum chamber being shaped and dimensioned to receive a human penis; and
- pumping means, at least part of which is mounted for reciprocation relative to the vessel, for pumping air out of the vacuum chamber.

The device may include seal means positioned in the vicinity of the mouth opening and configured sealingly to engage with an outer surface of a human penis inserted into the vacuum chamber.

The pumping means may include:

- a pumping member, mounted on and slidingly displaceable relative to the vessel, the vessel and pumping member being shaped and configured so that the vessel and the pumping member together form a suction chamber and so that sliding displacement of the pumping member and the vessel relative to one another changes the volume of the suction chamber;
- at least one pumping passage extending between the vacuum chamber and the suction chamber;
- at least one exhaust passage leading from the suction chamber;
- first one way valve means which permits fluid flow from the vacuum chamber to the suction chamber via the, or each, pumping passage; and
- second one way valve means which permits fluid to be discharged from the suction chamber via the or each exhaust passage to atmosphere.

The vessel may have an outer surface which is substantially cylindrical for at least part of its length, the pumping member extending around the cylindrical portion of the outer surface of the vessel and being longitudinally slidingly displaceable relative thereto.

The or each pumping passage may be positioned and the pumping member may be arranged so that displacement of the pumping member towards the mouth of the vessel increases the volume of the suction chamber and causes air to flow from the vacuum chamber through the or each pumping passage into the suction chamber and displacement of the pumping member away from the mouth of the vessel decreases the volume of the suction chamber and causes air to be discharged from the suction chamber through the exhaust passage to atmosphere.

As the vacuum drawn in the vacuum chamber increases it becomes more difficult to draw air out of the vacuum and the effort required to displace the pumping member in the direction required to increase the volume of the suction chamber increases. By arranging the pumping means such that the volume of the pumping chamber increases when the pumping member is displaced towards the mouth of the vessel the primary loads applied to the device, in use, are towards a user's body which helps to minimize any discomfort the user may experience.

The pumping vessel may have a cylindrical wall and the or each pumping passage may extend through the wall and have a mouth opening into the suction chamber, the first one way valve means being in the form of at least one elastically deformable band extending around the cylindrical wall to cover the or each mouth.

The second one way valve means may include an O-ring configured to provide an air tight seal between the pumping member and the vessel when being displaced relative to one another to increase the volume of the pumping chamber and to permit air to be discharged through the at least one exhaust passage when the pumping member and the vessel are being displaced relative to one another to decrease the volume of the pumping chamber.

In order to ensure the safe operation of the device it is desirable that the pressure in the vacuum chamber not decrease below a predetermined minimum pressure, typically of the order of −0.57 bar. However, the Inventor believes that a vacuum of −0.4 bar will work satisfactorily.

Accordingly, the device may include vacuum restriction means for restricting the vacuum which can be drawn in the vacuum chamber.

The vacuum restriction means may include a stroke limiting member positioned in the suction chamber to restrict the stroke through which the pumping member is displaceable relative to the vessel.

The seal means may include a sealing constriction ring which is readily dismountably mounted on the vessel in the vicinity of the mouth opening, the constriction ring including a generally ring-shaped body having a circumferentially extending engagement formation for releasable sealing engagement with the vessel in the vicinity of the mouth opening and a constriction ring opening configured sealingly to abut against the outer surface of a human penis.

The body of the constriction ring may be formed of a unitary moulding of an elastomeric material. In one embodiment of the invention the elastomeric material may be a silicone rubber and have a hardness of 50 A Shore.

The size of the constriction ring opening will depend on the intended application. Hence, where intended for use in the treatment of erectile dysfunction the opening will be sufficiently small to inhibit blood flow from the penis once an erection is attained in order to maintain the erection. In contrast, when the device is intended to be used for penile exercise the opening will be sufficiently small to seal against a surface of the penis and sufficiently large to permit blood to drain from the erect penis.

The constriction ring opening may have a diameter of between 13 and 24 mm.

The device may include a plurality of interchangeable sealing constriction rings each having a constriction ring opening of a different size.

According to another aspect of the invention there is provided a method of treating erectile dysfunction in the human male, which includes the steps of drawing a penis through a sealing constriction ring which is releasably mounted on a vessel into a vacuum chamber defined in the vessel by pumping air out of the vacuum chamber to draw the penis through the ring into the vacuum chamber and to cause an erection of the penis in the vacuum chamber; and disconnecting the sealing constriction ring from the vessel and removing the erect penis with the sealing constriction ring thereon from the vessel, the sealing constriction ring having a constriction ring opening which is small enough to constrict blood flow from the erect penis, thereby maintaining the erection.

Pumping air out of the vacuum chamber may include displacing a pumping member which is mounted on and displaceable relative to the vessel.

According to yet another aspect of the invention there is provided a method of penile exercise, which includes the steps of drawing the penis through a sealing constriction ring which is mounted on a vessel into a vacuum chamber defined in the vessel by pumping air out of the vacuum chamber by reciprocal displacement of a pumping member mounted on the vessel thereby to draw the penis through the ring into the vacuum chamber and to cause an erection of the penis in the vacuum chamber; and relieving the vacuum around the penis to permit blood to drain from the erect penis thereby relaxing the erection, the sealing constriction ring having an opening which is small enough to engage sealingly around the penis and large enough to permit blood to drain from the erect penis when the vacuum is relieved.

Relieving the vacuum may include breaking the seal between the sealing constriction ring and the vessel.

The Inventor believes the invention may find application in other pump devices.

Hence, according to still yet another aspect of the invention there is provided a pump device which includes a vessel defining a primary chamber;

a pumping member mounted on the vessel for reciprocation relative to the vessel, the pumping member and the vessel defining between them a secondary chamber, the volume of which changes when the pumping member is displaced relative to the vessel; and valve means whereby the primary chamber and the secondary chamber are selectively connectable in flow communication and whereby the secondary chamber is selectively connectable in flow communication with atmosphere.

The secondary chamber may be an annular chamber which extends around the vessel, the valve means including first one way valve means configured to connect the primary chamber in flow communication with the secondary chamber when the pumping member is displaced in a direction which increases the volume of the secondary chamber and second one way valve means configured to connect the secondary chamber in flow communication with atmosphere when the pumping member is displaced in the opposite direction. Reciprocation of the pumping member will thus cause the pressure inside the primary chamber to be reduced incrementally.

Hence, the pump device will function as a vacuum pump to draw a vacuum in the primary chamber.

The vessel may have an outer surface which is cylindrical for at least part of its length and the pumping member may be an at least partly cylindrical member which extends around at least part of the cylindrical surface of the vessel and which is longitudinally slidingly displaceable relative to the vessel.

Preferably the pumping member is a sleeve which encircles the cylindrical vessel for at least part of its length.

The invention extends to a constriction ring for use on a device as described above.

More particularly, the invention extends to a sealing constriction ring for use with a device including a vessel defining a vacuum chamber and having a mouth opening as hereinbefore described, the constriction ring comprising a generally ring-shaped body having a circumferentially extending engagement formation for releasable, sealing engagement with the opening and a constriction ring opening shaped and configured to sealingly engage with the outer surface of a zone around a human penis.

According to a further aspect of the invention there is provided a sealing constriction ring which includes a body of an elastomeric material, the body having a tubular central portion defining a constriction ring opening, a radially inner surface of the central portion forming a penis contacting surface for contacting an outer surface of a penis extending through the constriction ring opening in an air tight manner;

a ring shaped formation which is positioned outwardly of the central portion and which defines a radially inwardly directed annular surface whereby the sealing constriction ring is mountable on a vessel defining a vacuum chamber; and an annular connecting web connecting the central portion and the ring-shaped formation together.

The constriction ring opening may have a diameter of about 13 to 24 mm. Thus depending upon the diameter of the constriction ring opening and the diameter of the erect penis, the sealing constriction ring may provide a relatively air-tight seal around the penis and constrict blood flow from the penis or merely provide a relatively air-tight seal.

BRIEF DESCRIPTION OF THE SEVERAL VIEWS OF THE DRAWINGS

The invention will now be described, by way of non-limiting example, with reference to the accompanying diagrammatic drawings.

In the drawings.

DETAILED DESCRIPTION OF THE INVENTION

Figure 1:
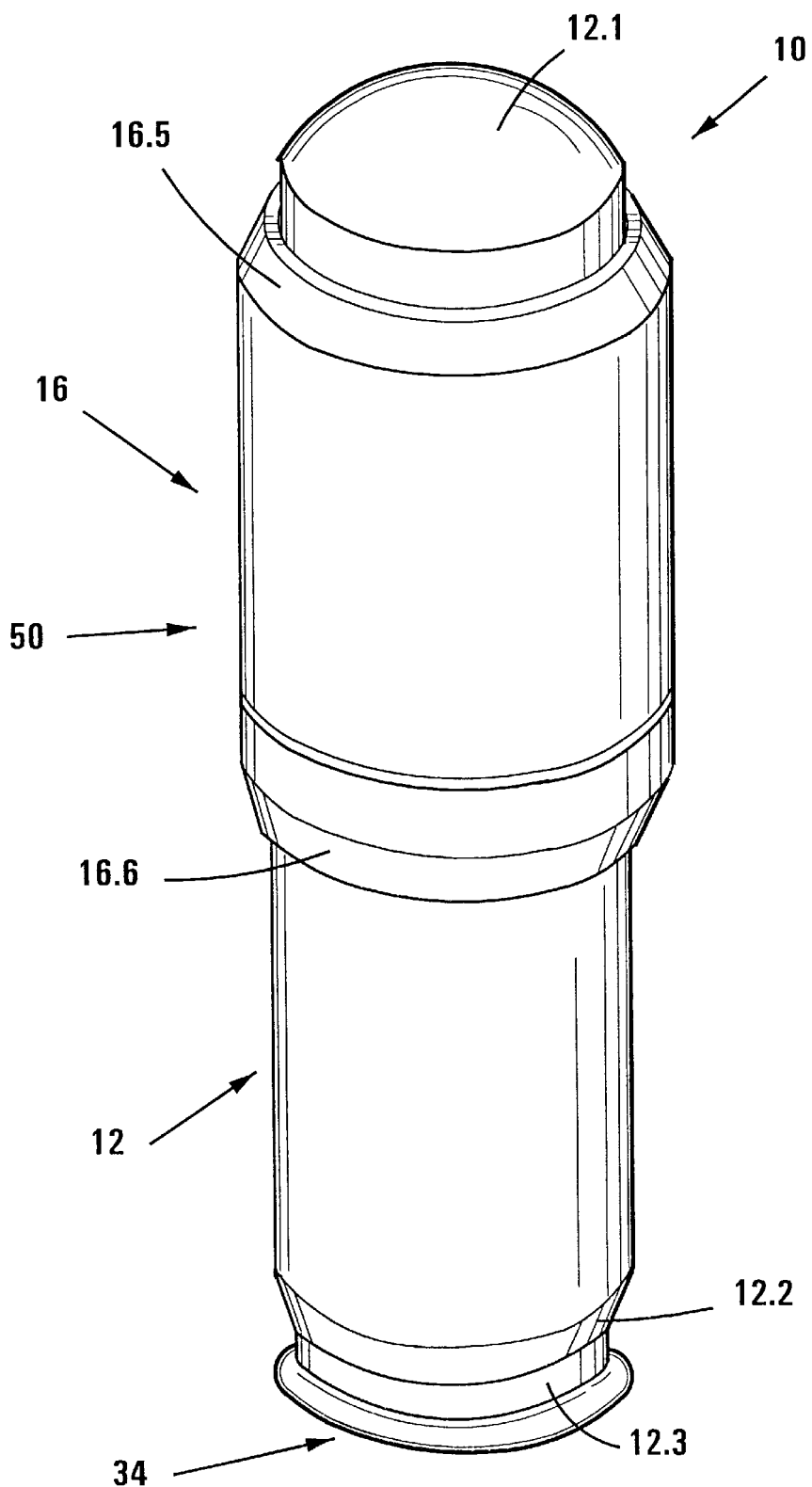
FIG. 1 shows a three-dimensional view of a device for the treatment of erectile dysfunction or for penile exercise in accordance with the invention.

Referring to FIGS. 1 to 4 of the drawings, reference numeral 10 generally indicates a device in accordance with the invention for use in the treatment of erectile dysfunction or for penile exercise.

Figure 3:
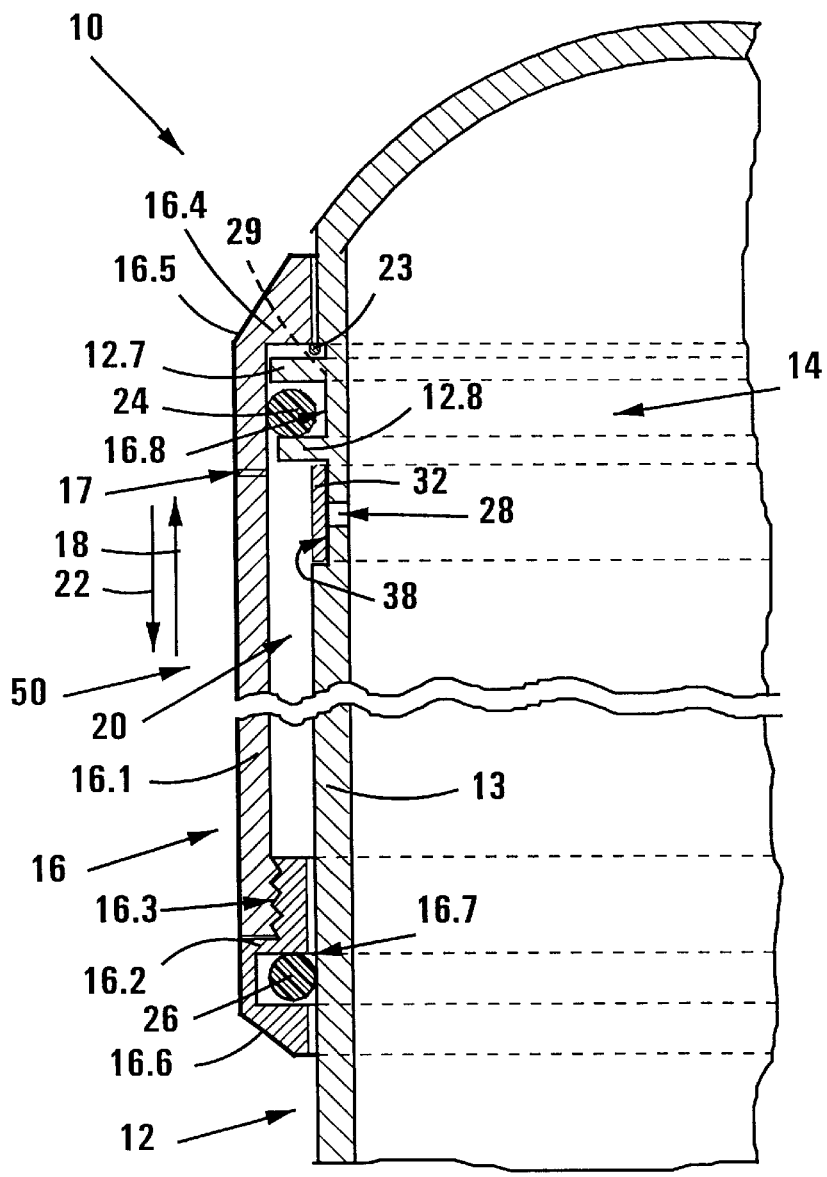
FIG. 3 shows a sectional side view of part of the device of FIG. 1.

The device 10 includes a hollow generally cigar shaped vessel 12 defining an elongate primary or vacuum chamber 14 (FIG. 3). The device 10 further includes pumping means, generally indicated by reference numeral 50 for pumping air out of the vacuum chamber 14.

Figure 2:
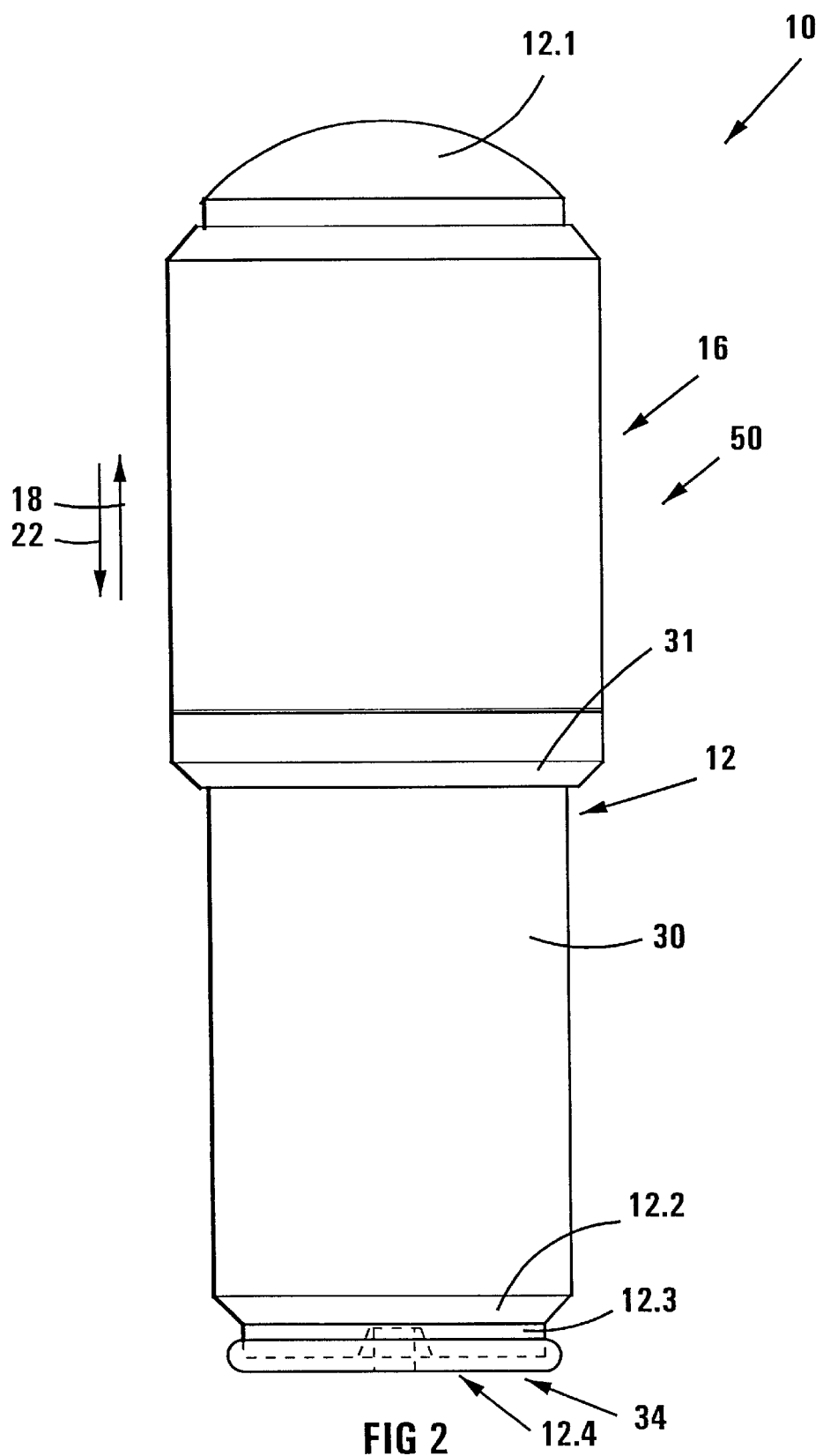
FIG. 2 shows a side view of the device of FIG. 1.

The vessel 12 has a generally cylindrical wall 13. The pumping means 50 includes a cylindrical pumping member or sleeve 16 which is mounted on and slidingly displaceable relative to the vessel 12 in the directions of the arrows 18, 22 (FIGS. 2 and 3). Referring, in particular, to FIG. 3 the vessel 12 and the sleeve 1 6 are configured so that, together, they form an annular secondary or suction chamber 20. As is also evident from FIG. 3, displacement of the pumping member in the direction of the arrow 22 will increase the volume of the suction chamber 20 and displacement in the direction of the arrow 18 will decrease the volume of the suction chamber 20. The pumping means 50 further includes sealing means in the form of a pair of O-rings 24, 26, described in further detail below, and pumping passages 28 in the wall 13 of the vessel 12 which provide a flow path for air to flow from the vacuum chamber 14 to the suction chamber 20. Four pumping passages 28 are provided, arranged in diametrically opposed pairs. the pumping means 50 includes upper exhaust passages, described in further detail below, indicated by the dotted lines 29 in FIG. 3 which allow air in the suction chamber 20 to be discharged to atmosphere when the pumping member 16 is moved in the direction of the arrow 18. The pumping means 50 further includes one way valve means in the form of a flat rubber band 32, described in further detail below, extending around the cylindrical vessel 12 to cover the pumping passages 28.

The vessel 12 has an open bottom end or mouth opening 12.4 (FIG. 2) which leads into an end of the vacuum chamber 14. Seal means in the form of a sealing constriction ring 34 is mounted on the vessel 12 in the vicinity of the mouth opening 12.4, as described in further detail below.

As can be seen, in particular, in FIG. 2, the cylindrical vessel 12 has a closed dome-shaped upper end 12.1 and a lower shoulder 12.2 adjacent the opening 12.4 with a narrower cylindrical part 12.3 extending from it and defining the opening 12.4.

As can be seen in FIG. 3, the sleeve 16 comprises a top part 16.1 and a bottom part 16.2 which are screw-threadedly joined by complementary screw threads generally indicated by reference numeral 16.3 with a lower portion of the upper part 16.1 overlapping an upper portion of the lower part 16.2 at the screw threads 16.3. This allows the device 10 to be disassembled. The upper part 16.1 has an upper inwardly directed collar 16.4 with a tapered upper face 16.5. The lower part 16.2 has a complementary tapered lower face 16.6. The lower part 16.2 has a circumferentially extending inwardly directed recess 16.7 and the O-ring 26 is positioned in the recess 16.7. The O-ring 26 is configured so that it sealingly and slidingly abuts the wall 13 of the cylindrical vessel 12 to provide an airtight seal between the vessel 12 and the pumping member or sleeve 16.

A collar 12.7 projects outwardly from the wall 13 below the inwardly directed collar 16.4 of the sleeve 16. The exhaust passages 29 are formed by spaced recesses in the collar 12.7. A second outwardly projecting collar 12.8 is located below the collar 12.7 and the wall 13 of the vessel 12 between the collars 12.7 and 1 2.8 is recessed. The collar 12.7 projects slightly further from the wall 13 of the vessel 12 than does the collar 12.8 as can be seen, in particular, in FIG. 3. This allows the sleeve 16 to slide smoothly over the collar 12.7 which thus acts as a guide for accurate "centering" of the sleeve 16. The collars 12.7, 12.8 define between them an annular cavity 16.8 and the O-ring 24 is positioned in the cavity 12.8. The O-ring 24 has a diameter which is selected so that it abuts slidingly and sealingly against the inside face of the sleeve 16. A further recessed portion 38 in the wall 13 of the vessel 12 is provided below the collar 12.8 and the pumping passages 28 extend through the wall 13 of the vessel 12 in the recessed portion 38. The rubber band 32 is located in the recessed portion 38 and covers the pumping passages 28. A vacuum relief hole 17 is provided in the top part 16.1 of the sleeve 16 adjacent the upper O-ring 24 to release vacuum when the sleeve 16 is in its lowest position.

A circumferentially extending rubber stop member 23 is provided above the collar 12.7 to dampen the sound of the sleeve when it is reciprocated.

Thus, in use, if the sleeve 16 is moved upwardly i.e. in the direction of the arrow 18, the O-ring 24 is displaced upwardly so that it abuts against the collar 12.7 and is clear of the collar 12.8. In addition, the volume of the exhaust chamber 20 is reduced and air in the exhaust chamber is driven past the O-ring 24 and the collar 12.8 and out through the exhaust passages 29. When the sleeve 16 is moved in the direction of the arrow 22, the O-ring 24 is displaced downwardly and abuts sealingly against the collar 12.8 thereby forming an airtight seal between the sleeve 16 and the vessel 12. In addition, the volume of the exhaust chamber 20 is increased so that air is sucked via the pumping passages 28, under and past the rubber band 32, which acts as a one way valve by allowing air flow from the vacuum chamber 14 to the suction chamber 20 but preventing air flow in the opposite direction. On the return stroke of the sleeve 16 air is again exhausted via the exhaust openings 29. The O-ring 24 hence functions as a one way valve. In this way by reciprocating movement of the sleeve 16, air is drawn out of the vacuum chamber 14 thereby, when the mouth is closed, incrementally reducing the pressure in the vacuum chamber 14. It will be appreciated that if desired the O-ring 26 can function as a one way valve in addition to the O-ring 24.

Figure 4:
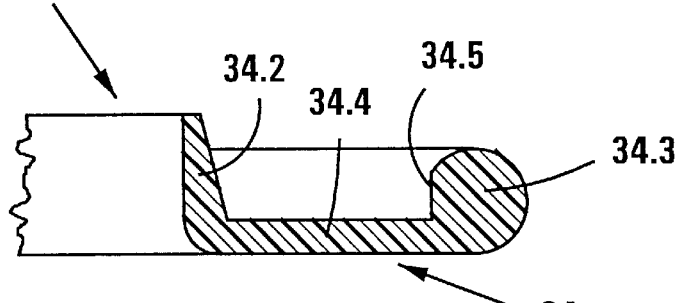
FIG. 4 shows, on an enlarged scale, a sectional side view of part of a sealing constriction ring forming part of the device of FIG. 1.

Referring now to FIG. 4 the constriction ring 34 comprises a body of rubber, e.g. silicone rubber. The ring 34 includes a central opening 34.1 surrounded by a tubular central portion or collar 34.2, a circumferentially extending upwardly directed ring-shaped formation or skirt 34.3 and a flat annular connecting web or recessed portion 34.4 between the collar 34.2 and the ring-shaped formation 34.3. The ring-shaped formation has an inner surface or wall 34.5. The outside diameter of the constriction ring 34 is about 58 mm. The diameter of the wall 34.5 is about 47 mm. This diameter is slightly smaller than the diameter of the cylindrical part 12.3 of the vessel 12 so that the constriction ring 34 is sealingly received or engaged on the end of the cylindrical part 12.3 of the vessel 12 by a friction fit. In different embodiments of the invention, the opening 34.1 has a diameter of 13 to 24 mm.

In use, the flaccid penis of a user (not shown) is drawn into the vessel 12 of the device 10 through the opening 34.1 of the constriction ring 34 by operating the sleeve 16 to reduce the air pressure in the pumping chamber 14 the penis is drawn into the vessel 12 and by virtue of the reduced pressure in the vacuum chamber 14 blood is drawn into the penis to achieve an erection of the penis in the vacuum chamber 14. The constriction ring 34 seats sealingly around the penis. The pumping action causes a pressure drop in the vacuum chamber 14 to about −0.4 bar. This is sufficient to draw the penis into the vessel 12 and to draw blood into the penis to cause an erection.

The skirt 34.2 is deformed by the drawing of the penis into the opening 34.1 thereby causing the seal-penis contact area to be increased by the draping of the skirt 34.2 onto the penis, collar-fashion. Once an erection is achieved, the vessel 12 is simply disengaged from the constriction ring 34 which remains in place on the erect penis. In this case the diameter of the opening 34.1 is selected by a user of the device 10 so that blood flow from the penis is constricted. In the case of penile exercise, the diameter of the opening 34.1 is selected by a user so that the constriction ring engages sealingly with the penis during the pumping action so that an erection is achieved but not so that blood flow from the penis is constricted when the vacuum is relieved. Thus when the vacuum is relieved blood flow from the penis relaxes the erection. Such penile exercise is believed to function as a treatment for erectile dysfunction.

In an embodiment of the invention (not shown), the vessel 12 is provided with a removable vacuum gauge for measuring the vacuum inside the vessel 12. Once a user is familiar with the use of the device, the vacuum gauge may be removed.

Figure 5:
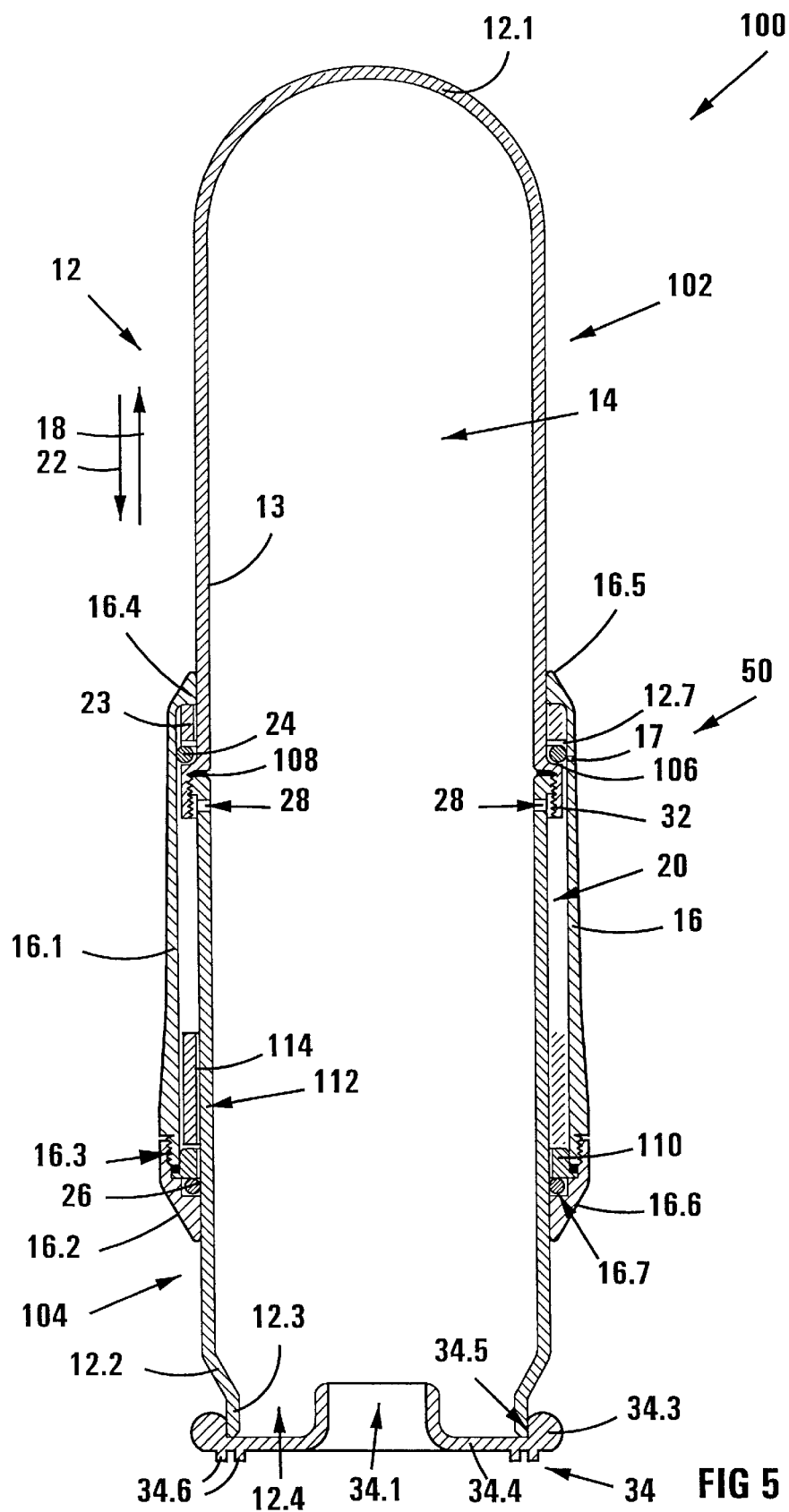
FIG. 5 shows a sectional side view of another device in accordance with the invention.

Reference is now made to FIG. 5 of the drawings, in which reference numeral 100 refers generally to another device in accordance with the invention for use in the treatment of erectile dysfunction or for penile exercise. Unless otherwise indicated, the same reference numerals used above are used to designate similar parts.

In this embodiment of the invention, the vessel 12 is formed in two parts 102 and 104 which are screw-threadedly connected together. The part 102 defines an annular shoulder 106, the O-ring 24 being held captive between the shoulder 106 and the collar 12.7. A seal 108 is provided between the two parts 102, 104.

The shoulder 106 functions in the same manner as the collar 12.8 of FIGS. 1 to 3 such that the O-ring 24 cooperates with the shoulder 106 to form a non-return or one way valve means. The O-ring 26 is held captive between the lower part 16.2 and an annular insert 110 which is sandwiched between the upper part 16.1 and the lower part 16.2 when they are screwed together. If desired, the lower part 16.2 and insert 110 can be configured such that the O-ring 26 also functions as a non-return valve.

This arrangement, the Inventor believes, will facilitate manufacture of the device 100.

In addition, the device 100 includes vacuum restriction means, generally indicated by reference numeral 112 for restricting the vacuum which can be drawn in the vacuum chamber 14. It will be appreciated that, in use, air will be drawn from the vacuum chamber 14 into the suction chamber 20 only when the pressure in the suction chamber 24 is below that in the vacuum chamber 14. Accordingly, by limiting the maximum vacuum which can be drawn in the suction chamber 20 the maximum vacuum which can be drawn in the vacuum chamber 14 is also limited. In order to achieve this, the vacuum restriction means 112 includes a stoke limiting member 114 which is positioned in the suction chamber 20 and is designed to limit the maximum stroke of the pumping member or sleeve 16 relative to the vessel 12. It is hence a relatively simple matter to calculate the stroke volume of the sleeve 16 and hence the maximum vacuum which can be drawn.

A further difference between the device 100 and the device 10 is that, in the case of the device 100 the pumping member or sleeve 16 is moved closer towards the mouth 12.4 and is arranged that at the extremities of its stroke it does not protrude beyond the ends of the vessel 12. This reduces the risk that an article of clothing or a body part may be caught between the sleeve 16 and the vessel 12.

In this embodiment of the invention, even though the sleeve 16 is moved closer to the mouth 12.4, at the limit of its pumping stroke, i.e. when closest to the mouth 12.4, the sleeve 16 is spaced from the mouth end of the vessel as shown in FIG. 5. This reduces the risk that the sleeve 16 will strike the testes or another part of the body of a user.

In addition, the diameter of the outer surface of the sleeve 16 increases towards the mouth 12.4. As mentioned above, the maximum effort applied to the sleeve 16 is when it is being displaced in the direction of arrow 22. Accordingly this gentle taper of the sleeve 16 reduces the risk that a user's hand will slip on the sleeve 16.

A further difference between the device 100 and the device 10 is that, in the case of the device 100, the sealing constriction ring 34 is provided with a pair of annular ribs or gripping formations 34.6 which assist in removing the ring 34 on the vessel 12.

The device 100 will be used in substantially the identical fashion to the device 10.

The Applicant believes that it is an advantage of the invention as illustrated that the device due to its size, form and simplicity of use can be easily used in an intimate situation. It is a particular advantage that the pumping vessel is easily detached from the constriction ring leaving the constriction ring in place.

The Applicant believes that it is a further advantage of the invention as illustrated that the sealing ring may be removably attached to the device to form a unit for ease of use.

What is claimed is:

1. A device for the treatment of erectile dysfunction or for penile exercise which includes:

a vessel having an outer surface which is substantially cylindrical for at least part of its length, the vessel defining a vacuum chamber and having a mouth opening leading into the vacuum chamber, the vacuum chamber being shaped and dimensioned to accommodate a human penis in an erect state; and pumping means which includes an annular pumping member mounted on and extending concentrically around the cylindrical portion of the outer surface of the vessel intermediate the ends thereof so that an annular suction chamber is defined between the outer surface of the vessel and the pumping member and vessel being slidingly displaceable relative to one another which relative displacement changes the volume of the suction chamber;

at least one pumping passage extending from the vacuum chamber, at a position intermediate the ends thereof, to the suction chamber;

at least one exhaust passage extending from the suction chamber;

first one way valve means which permits fluid flow from the vacuum chamber to the suction chamber via the, or each, pumping passage; and second one way valve means which permits fluid to be discharged from the suction chamber via the, or each exhaust passage to atmosphere.

2. A device as claimed in claim 1, which includes seal means positioned in the vicinity of the mouth opening and configured sealingly to engage with an outer surface of a human penis inserted into the vacuum chamber.

3. A device as claimed in claim 2, inclusive, in which the seal means includes a sealing constriction ring which is dismountably mounted on the vessel in the vicinity of the mouth opening, the constriction ring including a generally ring-shaped body having a circumferentially extending engagement formation for releasable sealing engagement with the vessel in the vicinity of the mouth opening and a constriction ring opening configured sealingly to abut against the outer surface of a human penis.

4. A device as claimed in claim 3, in which the sealing constriction ring is formed of a unitary moulding of an elastomeric material.

5. A device as claimed in claim 3, in which the constriction ring opening has a diameter of between 13 and 24 mm.

6. A method of treating erectile dysfunction in the human male, which includes the steps of
drawing a penis through the sealing constriction ring which ring is releasably mounted on the vessel into the vacuum chamber defined in the vessel of a device as claimed in claim 10 by displacing the pumping member relative to the vessel to pump air out of the vacuum chamber to draw the penis through the ring into the vacuum chamber and to cause an erection of the penis in the vacuum chamber; and
disconnecting the sealing constriction ring from the vessel and removing the erect penis with the sealing constriction ring thereon from the vessel, the sealing constriction ring having a constriction ring opening which is small enough to constrict blood flow from the erect penis, thereby maintaining the erection.

7. A device as claimed in claim 1, in which the or each pumping passage is positioned and the pumping member is arranged so that displacement of the pumping member towards the mouth of the vessel increases the volume of the suction chamber and causes air to flow from the vacuum chamber through the or each pumping passage into the suction chamber and displacement of the pumping member away from the mouth of the vessel decreases the volume of the suction chamber and causes air to be discharged from the suction chamber through the exhaust passage to atmosphere.

8. A device as claimed in claim 1, in which the vessel has a cylindrical wall and the or each pumping passage extends through the wall and has a mouth opening into the suction chamber, the first one way valve means being in the form of at least one elastically deformable band extending around the cylindrical wall to cover the or each mouth.

9. A device as claimed in claim 1, in which the second one way valve means includes O-ring configured to provide an air tight seal between the pumping member and the vessel when being displaced relative to one another to increase the volume of the pumping chamber and to permit air to be discharged through the at least one exhaust passage when the pumping member and the vessel are being displaced relative to one another to decrease the volume of the pumping chamber.

10. A device as claimed in claim 1, which includes vacuum restriction means for restricting the vacuum which can be drawn in the vacuum chamber.

11. A device as claimed in claim 10, in which the vacuum restriction means includes a stroke limiting member positioned in the suction chamber to restrict the stroke through which the pumping member is displaceable relative to the vessel.

12. A method of penile exercise, which includes the steps of
drawing the penis through a sealing constriction ring which is mounted on a vessel into a vacuum chamber defined in the vessel by pumping air out of the vacuum chamber by reciprocal displacement of a pumping member mounted on the body thereby to draw the penis through the ring into the vacuum chamber and to cause an erection of the penis in the vacuum chamber; and
relieving the vacuum around the penis by breaking the seal between the sealing constriction ring and the vessel to permit blood to drain from the erect penis thereby relaxing the erection, the sealing constriction ring having an opening which is small enough to engage sealingly around the penis and large enough to permit blood to drain from the erect penis when the vacuum is relieved.

13. A method as claimed in claim 12, in which relieving the vacuum includes disconnecting breaking the seal between the sealing constriction ring and the vessel.

14. A pump device which includes
an elongate vessel defining a primary chamber;
the pumping member mounted on the vessel for reciprocation relative to the vessel, the pumping member and the vessel defining between them a secondary chamber, the volume of which changes when the pumping member is displaced relative to the vessel, and being configured such that at the extremities of its stroke, the pumping does not protrude beyond the ends of the vessel; and
valve means whereby the primary chamber and the secondary chamber are selectively connectable in flow communication and whereby the secondary chamber is selectively connectable in flow communication with atmosphere.

15. A pump device as claimed in claim 14, in which the secondary chamber is an annular chamber which extends around the vessel, the valve means including first one way valve means configured to connect the primary chamber in flow communication with the secondary chamber when the pumping member is displaced in a direction which increases the volume of the secondary chamber and second one way valve means configured to connect the secondary chamber in flow communication with atmosphere when the pumping member is displaced in the opposite direction.

16. A sealing constriction ring which includes a body of an elastomeric material, the body having
a tubular central portion defining a constriction ring opening, a radially inner surface of the central portion forming a penis contacting surface for contacting an outer surface of a penis extending through the constriction ring opening in an air tight manner;
a ring shaped formation which is positioned outwardly of the central portion and which defines a radially inwardly directed annular circular-cylindrical surface whereby the sealing constriction ring is mountable on a vessel defining a vacuum chamber so that the circular-cylindrical surface sealingly engages a complementary surface of a said vessel; and
an annular connecting web connecting the central portion and the ring-shaped formation together.

17. A device for the treatment of erectile dysfunction or for penile exercise which includes: an elongate vessel defining a vacuum chamber, the vessel being closed at one end and having at its other end a mouth opening leading into the vacuum chamber, the vacuum chamber being shaped and dimensioned to accommodate a human penis; and pumping means for pumping air out of the vacuum chamber, the pumping means including a pumping member, mounted on and longitudinally slidingly displaceable relative to the vessel such that at the extremities of its stroke, the pumping member does not protrude beyond the ends of the vessel.

18. A device as claimed in claim 17, in which includes seal means positioned in the vicinity of the mouth opening and configured sealingly to engage with an outer surface of the human penis inserted into the vacuum chamber.

19. A device as claimed in claim 17, in which the vessel and pumping means are shaped and configured so that the vessel and pumping member together form a suction chamber and so that sliding displacement of the pumping member and the vessel relative to one another changes the volume of the suction chamber, the pumping means including:

at least one pumping passage extending between the vacuum chamber and the suction chamber;

at least one exhaust passage leading from the suction chamber;

first one way valve means which permits fluid flow from the vacuum chamber to the suction chamber via the, or each, pumping passage; and second one way valve means which permits fluid to be discharged from the suction chamber via the or each exhaust passage to atmosphere.

\* \* \* \* \*